United States Patent
Lawlis et al.

(10) Patent No.: US 7,354,395 B2
(45) Date of Patent: **\*Apr. 8, 2008**

(54) METHODS AND APPARATUS FOR ACOUSTICAL STIMULATION OF THE BRAIN

(76) Inventors: G. Frank Lawlis, 1690 Lawlis La., Sanger, TX (US) 76266-0034; T. Frank Lawlis, 1909 St. James Rd., Pilot Point, TX (US) 76258

( * ) Notice: Subject to any disclaimer, the term of this patent is extended or adjusted under 35 U.S.C. 154(b) by 0 days.

This patent is subject to a terminal disclaimer.

(21) Appl. No.: 11/424,653

(22) Filed: Jun. 16, 2006

(65) Prior Publication Data

US 2006/0224036 A1    Oct. 5, 2006

Related U.S. Application Data

(63) Continuation of application No. 10/652,630, filed on Aug. 29, 2003, now Pat. No. 7,166,070.

(51) Int. Cl.
   *A61M 21/00*   (2006.01)
(52) U.S. Cl. ...................................... 600/28
(58) Field of Classification Search ............ 600/26–28, 600/544–545
   See application file for complete search history.

(56) References Cited

U.S. PATENT DOCUMENTS

| | | | |
|---|---|---|---|
| 3,712,292 A | 1/1973 | Zentmeyer, Jr. | |
| 3,884,218 A | 5/1975 | Monroe | |
| 4,141,344 A | 2/1979 | Barbara | |
| 4,191,175 A | 3/1980 | Nagle | |
| 4,227,516 A | 10/1980 | Meland et al. | |
| 4,228,807 A | 10/1980 | Yagi et al. | |
| 4,289,121 A | 9/1981 | Kupriyanovich | |
| 4,315,502 A | 2/1982 | Gorges | |
| 4,334,545 A | 6/1982 | Shiga | |
| 4,335,710 A | 6/1982 | Williamson | |
| 4,335,716 A | 6/1982 | Stephen et al. | |
| 4,388,918 A | 6/1983 | Filley | |
| 4,573,449 A | 3/1986 | Warnke | |
| 4,834,701 A | 5/1989 | Masaki | |
| 4,883,067 A | 11/1989 | Knispel et al. | |
| 5,036,858 A | 8/1991 | Carter et al. | |
| 5,123,899 A | 6/1992 | Gall | |
| 5,885,976 A | 3/1999 | Sandyk | |
| 5,954,630 A | 9/1999 | Masaki et al. | |
| 6,135,944 A | 10/2000 | Bowman et al. | |
| 6,409,655 B1 | 6/2002 | Wilson et al. | |
| 7,150,526 B2 * | 12/2006 | Jannard et al. ............. | 351/158 |
| 7,166,070 B2 * | 1/2007 | Lawlis et al. ................. | 600/28 |

OTHER PUBLICATIONS

Jacobs, Aaron, Clinical study: BAUD assisted neurotherapy, Nov. 11, 2004, University of North Texas.
Lawlis, Frank, The ADD Answer: How to Help Your Child Now, Aug. 19, 2004, pp. 179-182, Viking Adult, USA.

* cited by examiner

*Primary Examiner*—John P Lacyk
(74) *Attorney, Agent, or Firm*—Locke Lord Bissell & Liddell LLP

(57) ABSTRACT

A method and apparatus is presented for acoustically stimulating the brain by generating primary and secondary acoustical signals having differing characteristics. The signal differential thereby creates a tertiary signal or third wave. A user is able to interactively adjust the characteristics of the third wave by adjusting the characteristics of the primary and/or secondary signals to benefit or ameliorate a specific human condition.

11 Claims, 2 Drawing Sheets

METHODS AND APPARATUS FOR ACOUSTICAL STIMULATION OF THE BRAIN

CROSS REFERENCE TO RELATED APPLICATIONS

This application is a continuation of U.S. application Ser. No. 10/652,630, filed on Aug. 29, 2003, now U.S. Pat. No. 7,166,070.

BACKGROUND OF THE INVENTION

Researchers have coined the term "Energy Medicine" to describe the interaction of various forms of energy, such as, for example, electric, magnetic, thermal, and acoustic energy with the functions of the body. Historically, most research has been focused on the use of electric energy and acoustic energy to control, induce or entrain brain waves or states benefiting conditions such as Attention Deficit Disorder, Epilepsy, Stroke, and Parkinson's disease, to name a few, or to enhance intellectual performance and concentration.

It has heretofore been demonstrated that human brain waves and activity can be entrained or affected by specific acoustic stimulation. Similarly, the beneficial effects of acupuncture and acupressure, also including crystal and magnetic stimulation, have been documented on a number of medical conditions, principally pain and anxiety. The present invention builds upon the previous efforts that have, among other things, researched areas of the body that are susceptible to Energy Medicine stimulation for the various organs and muscle groups as well as previous efforts that have researched the acoustical or vibrational waveforms related to physical, emotional and mental health.

SUMMARY OF THE INVENTION

The present invention, as set forth in the appended claims, may be summarized as a stimulation system comprising a signal generator capable of generating at least two acoustic signals, each having a frequency of about 0.1 Hz to about 4,000 Hz. The system includes a user interface that communicates with the signal generator and provides a user the capability to adjust the frequency and volume of at least one of the two signals. Also included are first and second ear pieces adapted to reside about the user's ears and each comprising a transducer for converting the signal into acoustic energy for stimulating the brain to a desired state of activity.

Further, the present invention comprises a user control for the beat of the signals and the ability of the user to set up the two signals with different volume, tone and/or beat characteristics. In such circumstances, the present invention creates with the brain a third tone or signal based on the mismatch or differential of the signals characteristics.

Further, the present invention comprises a method by which a user can interactively determine the best combination of primary, secondary and tertiary signal characteristics to benefit or ameliorate a particular condition or circumstance.

Other aspects of the present invention can be gleaned from the following description of an embodiment utilizing the apparatus of the invention and the appended claims.

DESCRIPTION OF ILLUSTRATIVE EMBODIMENTS

Figure 1:
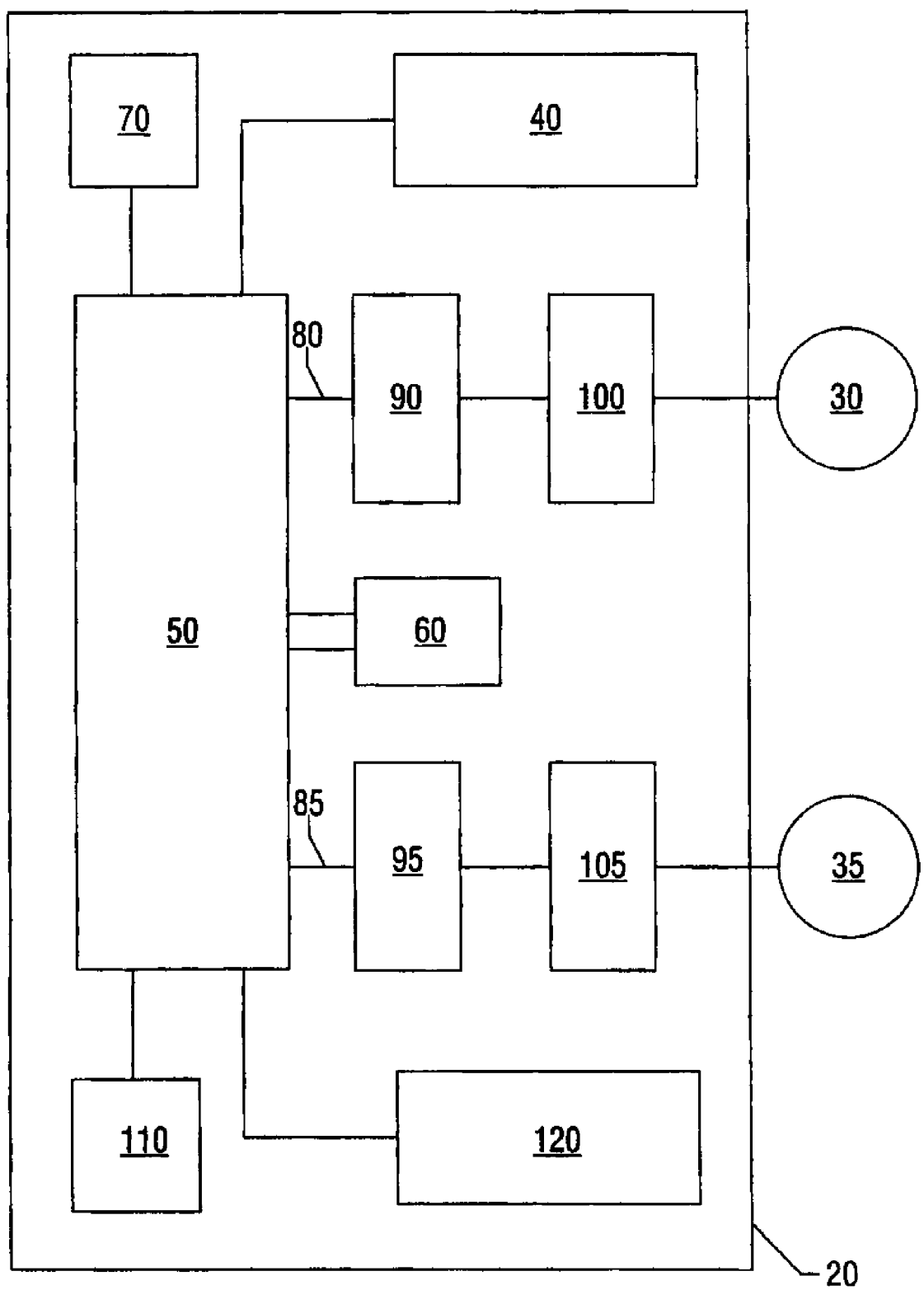
FIG. 1 illustrates a stimulator system utilizing the present invention.

The present invention and its use is disclosed herein by describing a specific embodiment utilizing the invention. By describing this specific embodiment in detail, those of ordinary skill in the art will come to appreciate and understand the broader aspects of the present invention and that the present invention is not limited to the specific embodiment detailed herein.

In perhaps its simplest form, the present invention may be utilized as a user-controllable device adapted to stimulate the auditory receptors in the human body and/or to stimulate energy sensitive receptors or centers in or on the body (e.g., acupuncture and acupressure points, crystal and/or magnetic points). The present invention may be implemented by generating a stimulation signal for each ear, which signals may be independent from or dependent upon one another. The user of the embodiment is provided utilities to adjust the volume, frequency or tone, and beat of the signals, including independent adjustment for each signal. The stimulation signals are converted by transducers worn about or in the ear into acoustical stimulation of the brain and, therefore, the body. One or more of crystal, magnetic and acupuncture/acupressure therapies may be combined with the acoustical stimulation system.

The present invention is not limited to a single embodiment or single mode of stimulation. Rather, the present invention operates more similarly to the complex operation of the human body. It is believed that the present invention works with four integrated systems in order to effect neurological and overall physical harmonization of body functions. The four systems are 1) brain wave activities related to emotional states; 2) acoustical stimulation of the related physiological systems; 3) the therapeutic effects of acupuncture and/or acupressure stimulation including also crystal and magnetic stimulation; and 4) the psychological impact of user control over personal stimulation.

The present invention comprises supplying a primary or dominant stimulation signal to one ear, preferably, but not exclusively, the left ear, and a secondary or subservient stimulation signal to the other ear. To the extent that the two signals are independent and different, a tertiary signal or "third wave" is set up or created based on the differential between the primary and secondary signals. It is believed that brain wave patterns respond to this tertiary signal. Applicant has observed that the brain tends to respond to the loudest of the primary and secondary stimulation signals and that the resulting third wave stimulates the brain into rapid shifts and alters the emotional relationships of the mental content. For example, it has been found that if a person is focused on studying for an exam and is anxious, the mental content is the subject of the exam and the emotional relationship is the feeling of anxiety. Within a relatively brief period of receiving acoustic stimulation including primary, secondary and tertiary stimulation signals, the person may be focusing on the exam with optimism and positive anticipation. Thus, the present invention can be implemented to modify the emotional relationship that is coupled to a specific task or condition. In practice, the dominant stimulation signal may be targeted to the major body system of focus, and the subservient stimulation signal may integrate the targeted body system with the rest of the body.

As discussed more fully below in terms of the presently preferred embodiment, the present invention may be implemented to interact with some or all of a user's body systems. The clinical applications for such an embodiment are unlimited. Presently, applicant envisions the clinical areas to which the present invention has particular application include, but are not limited to: addictions, e.g., alcohol, smoking, and food; anxiety; attention deficit disorder, e.g., ADD, ADHD; autoimmune disorders, e.g., arthritis, M.S., diabetes; cardiovascular disorders, e.g. hypertension; chronic spinal pain; depression; and enhanced intellectual performance.

Embodiments of the present invention may be constructed using simple analog circuits and components, microprocessor-based systems, software systems and/or any combination of these. It is contemplated that the present invention may be implemented in dedicated devices designed and manufactured specifically for the purposes contemplated herein, or as an add-on to existing platforms. For example, implementation of the present invention may be based upon Pocket PC or Palm Pilot-type platforms, including, for example cell phones.

One embodiment utilizing the present invention is illustrated in FIG. 1. A stimulation system 10 is shown, which comprises a stimulator 20 and earpieces 30 and 35. The stimulator 20 comprises a user interface section 40, a microprocessor-based signal generator 50 and a power supply section 60. The signal generator 50 may be any of a number of analog circuits or integrated circuits, but in the embodiment shown in FIG. 1, the signal generator 50 is a Microchip Technology, Inc. PIC18F452 micro controller. The signal generator 50 has an associated crystal 70 for timing the microprocessor, which in this embodiment is a 9.8304 MHz crystal. The signal generator 50 is capable of outputting two pulse code modulated (PCM) sine waves 80 and 85, which are inputted to signal conditioning sections 90 and 95, respectively. Signal conditioning sections 90 and 95 are conventional in the art and condition the sine waves 80 and 85 for amplification by amplifier sections 100 and 105. The amplified signals are then communicated to left and right ear pieces 30 and 35. FIG. 1 also illustrates configuration device 110, such as jumper pins or dip switches for providing some functional control over system 10. A communication section 120 is provided for communicating with the micro controller, such as for downloading programs into the micro controller's memory for specific conditions. In the embodiment shown in FIG. 1, the communication section 120 comprises an RS-232 interface.

Figure 2:
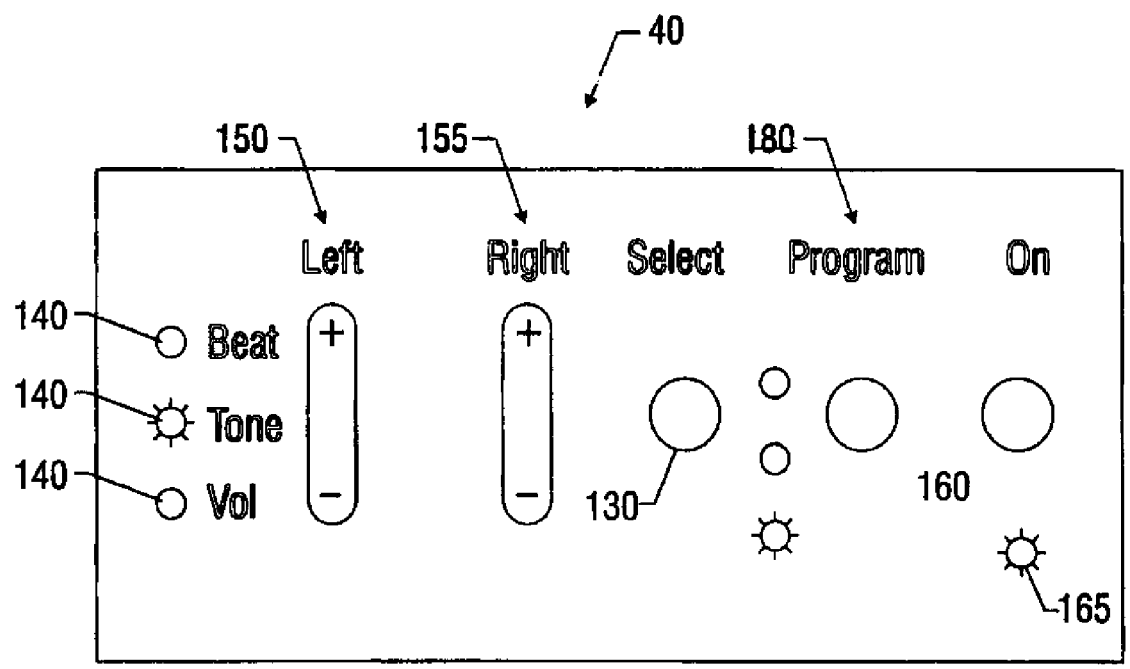
FIG. 2 illustrates a user interface for use with the stimulator system of FIG. 1.

FIG. 2 illustrates more specifically the user interface section 40 of FIG. 1. In the embodiment illustrated in FIG. 1, user interface 40 has user adjustable controls for volume, tone and beat. The embodiment shown in FIG. 2 uses a select switch 130 to cycle the user control through the parameters of volume, tone and beat. LEDs 140 or other visual indicators are provided to indicate which parameter may be changed. Left and right switches 150 and 155 are provided so that the user can increase or decrease the selected parameter. For example, as the user repeatedly depresses selector switch 130, the LEDS corresponding to volume, tone and beat light up sequentially. When the tone LED is lit, the user may increase or decrease the frequency (tone) of the left ear piece signal by manipulating switch 150 accordingly. Similarly, the tone of the right ear piece signal may be increased or decreased by manipulating switch 155 accordingly. An on/off switch 160 and corresponding "on" LED 165 are also provided.

Referring back to FIG. 1, the signal generator 50 is capable of producing a PCM sine wave that may be selectively varied from about 0.1 Hz to about 4 kHz. The signal generator 50 can also impose a beat on the PCM sine wave ranging in frequency from about 0.5 Hz to about 1 kHz, and preferably about 1 Hz to about 10 Hz. For example, the stimulator system 10 can generate or create stimulation for specific brain bands, such as 16-24 Hz for the beta state involving active problem solving and concentration; 8-12 Hz for the Alpha state involving calmness and focus; 4-7 Hz for the theta state involving imagery and creativity; and 0.5-3 Hz for the delta state involving sleep.

Figure 3:
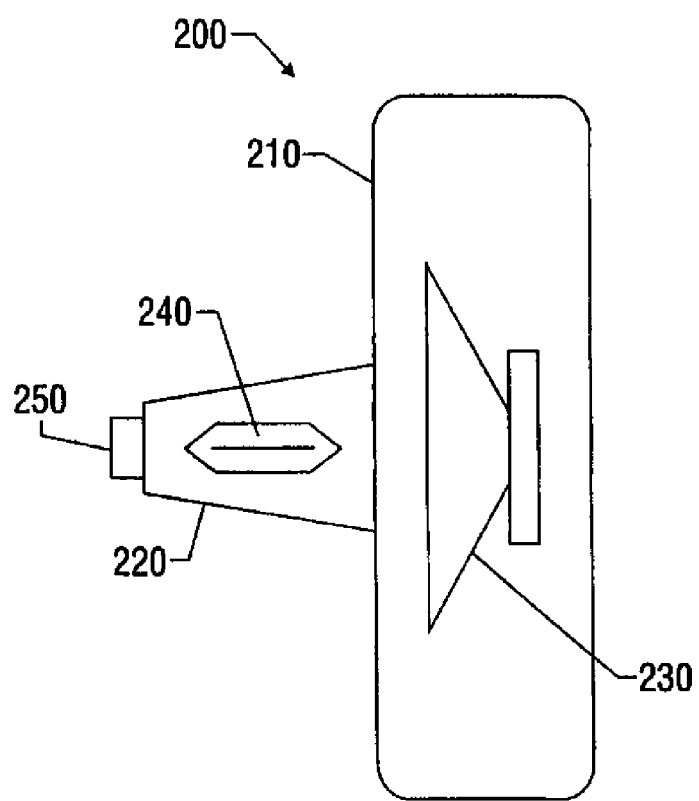
FIG. 3 illustrates an earpiece for use with the stimulator system of FIG. 1.

The signal generator 50 generates signals that, when applied to their respective transducer earpiece 30 or 35, produce the desired acoustic stimulation. FIG. 3 illustrates an embodiment of an ear piece for use with devices employing the present invention. Ear piece 200 comprises a body 210 having a protuberance 220 design to nestle in a portion of the outer ear canal (not shown). Transducer 230 may be a conventional headphone-type transducer that converts the electric signal from the stimulator 20 into acoustical energy or sound pressure waves. Additionally, the ear piece 200 may comprise a crystal 240 and/or magnet 250 to enhance the stimulation of the body.

Also shown in FIG. 1 is a configuration device 110, which communicates with the signal generator 50. Configuration device 110 may be used to control which of a plurality of stimulation programs the signal generator section 50 may use. A specific configuration of dip switches or jumpers in configuration device 110 may allow signal generator 50 to only generate signals 80 and 85 within a predetermined therapeutic or beneficial range for the condition being treated. For example, for a lay user seeking treatment of attention deficit, hyperactivity disorder (ADHD), configuration device 110 can be set to only permit signal generator section 50 to generate signals that will create, upon transduction by the ear pieces, stimulation within the therapeutic or beneficial range previously determined for that user or for that condition. In other words, in the embodiment shown in FIG. 1 configuration device 110 may be employed to limit the control that user interface section 40 provides.

In the embodiment illustrated in FIG. 1, the stimulation system 10 can be used for a plurality of conditions by setting and/or resetting configuration device 110 accordingly. Resetting may be accomplished, depending on the design of stimulation system 10, by changing a set of jumper wires or dip switches 110, or by loading condition-specific software (not shown) via the RS-232 communication section 120. In the case of jumper wire or dip switches 110, it is contemplated that the stimulation system 10 would be pre-loaded with a plurality of programs for the various treatable conditions. In the case of software programming, individual programs may be loaded into the memory of the signal generator 50 one at a time or previously loaded programs may be activated. Of course, the present invention also permits a stimulation system 10 to provide a plurality of programs (e.g., alcohol addiction, ADHD and depression) to the user based on the condition of a user selectable program switch 180 (FIG. 2) on user interface 40 (FIG. 2).

It is contemplated that a lay user would purchase a stimulation system 10 pre-programmed for a specific condition, such as alcohol addiction, and the user would not be permitted to change the programming (i.e. the treated condition) without approval from the vendor. Further, it is contemplated that the system 10 may utilize a timer or use function that records or otherwise logs the amount of time or number of uses to which the stipulation system 10 has been subjected. When such time of use or amount of usage reaches a preset limit, the stimulation system 10 would be rendered inoperative by a lock-out feature until and unless the user renews the system 10 with the vendor. In the embodiment shown in FIG. 1, such lock-out feature may be programmed into the micro controller.

It is contemplated that wired or wireless data communication may be utilized to program, re-program and/or renew the system 10. For example, upon purchase or lease of the system 10 from an authorized vendor, the sales agent may utilize conventional wired or wireless communication technology (not shown) to install the desired program into the micro controller and set the timer/lock-out feature to, for example, 60 uses or 30 days, which ever event first occurs. Upon occurrence of the lock-out event, the user would call an authorized vendor or log on to an authorized web site, which vendor site would use wired or wireless data communication to either reset the lock-out feature 300 or load a different program into system 10.

In use, the user will turn on the system 10 by activating the power switch 160. If provided, the user will then select the appropriate program by depressing switch 180 until the appropriate program is selected as indicated by the corresponding LED. Thereafter, the user will adjust the user controls 130, 150 and 155 as desired to achieve the desired level and effect of stimulation. The user is able to select the "best" tone (frequency) for each of the primary and secondary signals, and therefore, the signal tertiary by manually adjusting the frequency controls in user interface section 40. In most applications, it is contemplated that the user will create a tertiary signal or by creating a frequency mismatch or differential between the left and right ears. For example, if the user sets the tone of the right ear at 450 Hz and the tone of the left ear at 525 Hz, a tertiary signal or frequency mismatch of 75 Hz will be created. In addition, the user may adjust the beat or pulse of the primary and secondary signals, which may be likened to the beat of a drum, by adjusting the beat controls.

The embodiment thus far described has utilized what may be called a simple or single PCM sine wave for each ear. Those of skill in the art will now appreciate that the present invention contemplates the generation of composite sine waves for each ear or for only one ear. For example, instead of the single, simple sine wave generated for the left ear, as described with respect to FIG. 1, stimulation system 10 may be adapted to create several sine waves of differing frequency and/or phase to form a composite stimulation signal. Such composite signal could exhibit timbre or "voice," also known as overtones. Such composite signal may be beneficial for certain conditions and ailments.

Further, stimulation system 10 may generate different stimulation signals sequentially to affect multiple conditions or ailments at one time. For example and using the left ear/left channel as an example, stimulation system 10 may be adapted to produce a compound left channel stimulation signal in which the first or first several beats or pulses comprise a simple or composite signal directed toward ameliorating ADHD. The next beat or the next several beats may comprise a simple or composite signal whose characteristics are directed toward ameliorating excessive weight gain. Based on the disclosure of the embodiment shown in FIGS. 1 and 2, those of ordinary skill will now appreciate the modifications that may be made to stimulator 10 and, particularly, to signal generator 50 and user interface 40 to accommodate these alternate modes of stimulation.

The present invention may be utilized by lay users as well by trained professionals, such as doctors, health researchers and the like. When professionals use the present invention with their patients or customers, the implementation may allow the professional complete access to the full range of stimulation disclosed herein, rather than being limited to targeting a specific condition or ailment. In addition, the professional implementation may include biofeedback, such as heart rate, blood pressure, oxygen saturation, heart rhythm, temperature, to name just a few. The feedback may be of the open loop variety in which the professional would monitor the biofeedback parameter and adjust the stimulation accordingly. Alternately, the feedback may be of the closed loop variety in which the biofeedback parameter is utilized by the stimulation system to automatically adjust one or more of the adjustable parameters, such as tone, volume, or beat.

Although the embodiment disclosed in FIGS. 1 and 2 allows adjustment of the primary and secondary signals to establish the characteristics of the third wave, the present invention may be implemented such that the user adjusts the primary signal (or the secondary signal) and the differential between the primary and secondary signals directly.

Turning now to the specifics of the stimulation signals, Applicants have found the following programs to be beneficial for the listed conditions and ailments.

Attention Deficit Disorder: A primary frequency of about 60-66 Hz and a secondary frequency selected to create a tertiary signal of about 33-42 Hz. The beat of the primary and the secondary signals may be selected by the user for best effect.

Attention Maintenance: A primary frequency of about 56-61 Hz and a secondary frequency selected to create a tertiary signal of about 37-44 Hz. The beat of the primary and/or secondary signals may be selected by the user for best effect.

Eating Disorders: A primary frequency of about 55-65 Hz and a secondary frequency selected to create a tertiary signal of about 37-45 Hz. The beat of the primary and/or secondary signals may be selected by the user for best effect.

Weight Wellness: To help each individual achieve the healthy weight for their body, a primary frequency of about 56-61 Hz and a secondary frequency selected to create a tertiary signal of about 72-93 Hz. The beat of the primary and/or secondary signals may be selected by the user for best effect.

Depression: A primary frequency of about 40-61 Hz and a secondary frequency selected to create a tertiary signal of about 16-25 Hz. The beat of the primary and/or secondary signals may be selected by the user for best effect.

Anxiety: A primary frequency of about 37-42 Hz and a secondary frequency selected to create a tertiary signal of about 27-32 Hz. The beat of the primary and/or secondary signals may be selected by the user for best effect.

Chronic Pain: A primary frequency of about 42-56 HZ and a secondary frequency selected to create a tertiary signal of about 12-32 Hz. The beat of the primary and/or secondary signals may be selected by the user for best effect.

Acute Pain: A primary frequency of about 33-370 Hz and a secondary frequency selected to create a tertiary signal of about 31-350 Hz. The beat of the primary and/or secondary signals may be selected by the user for best effect.

Addictions: A primary frequency of about 24-32 Hz and a secondary frequency selected to create a tertiary signal of about 12-18 Hz. The beat of the primary and/or secondary signals may be selected by the user for best effect.

Sleep Disorders: A primary frequency of about 8-12 Hz and a secondary frequency selected to create a tertiary signal of about 2-4 Hz. The beat of the primary and/or secondary signals may be selected by the user for best effect.

Iatrogenic Pain: Pain that is due to medical procedures and interventions may find relief with a primary frequency of about 12-56 Hz and a secondary frequency selected to create a tertiary signal of about 10-46 Hz. The beat of the primary and/or secondary signals may be selected by the user for best effect.

Parkinsons: A primary frequency of about 100-210 Hz and a secondary frequency selected to create a tertiary signal of about 55-180 Hz. The beat of the primary and/or secondary signals may be selected by the user for best effect.

Alzheimers: A primary frequency of about 100-120 Hz and a secondary frequency selected to create a tertiary signal of about 55-75 Hz. The beat of the primary and/or secondary signals may be selected by the user for best effect.

Hypertension: A primary frequency of about 56-61 Hz and a secondary frequency selected to create a tertiary signal of about 52-55 Hz. The beat of the primary and/or secondary signals may be selected by the user for best effect.

Diabetes: A primary frequency of about 64-68 Hz and a secondary frequency selected to create a tertiary signal of about 40-55 Hz. The beat of the primary and/or secondary signals may be selected by the user for best effect.

Sexual Issues: A primary frequency of about 45-50 Hz and a secondary frequency selected to create a tertiary signal of about 33-38 Hz. The beat of the primary and/or secondary signals may be selected by the user for best effect.

Stress: A primary frequency of about 20-32 Hz and a secondary frequency selected to create a tertiary signal of about 12-15 Hz. The beat of the primary and/or secondary signals may be selected by the user for best effect.

Applicants envision that the present invention and its method of use would not supplant the current treatment or protocol to which a user has been referred, although such may be the case in specific instances. Rather, applicants envision the present invention and its method of use as a supplement or adjuvant.

Having described a specific embodiment utilizing the aspects of the present invention, applicant claims protection for his invention as set forth in the following claims:

What is claimed is:

1. A device, comprising:
   a signal generator adapted to generate at least two sounds each having a frequency in the range of about 0.1 hertz to about 4,000 hertz;
   a user interface coupled to the signal generator and providing adjustment of at least the frequency and volume of at least one of the two sounds; and
   a transducer adapted to transmit the at least two sounds to the brain of the user to thereby stimulate the brain into a desired state of activity without regard to the then-current brain wave activity of the user.

2. The device of claim 1, further comprising the ability to adjust a beat of at least one of the sounds from about 0.5 hertz to about 1,000 hertz.

3. The device of claim 1, wherein the beat of the at least one sound can be adjusted from about 1 hertz to about 10 hertz.

4. The device of claim 1, wherein at least one of the sounds comprises a simple sine wave and the other sound comprises a composite sine wave having frequency overtones.

5. The device of claim 1, wherein the sounds are selected from the group consisting of: a simple sine wave, a composite sine wave, a compound sine wave and any combination of the foregoing.

6. The device of claim 1, wherein the signal generator is programmable.

7. The device of claim 6, wherein the device can be programmed or reprogrammed by wired or wireless data transmission.

8. The device of claim 1, wherein the signal generator can be programmed to generate specific ranges of brain activity.

9. The device of claim 1, wherein the signal generator is programmed to create a range of brain activity that benefits or ameliorates a condition selected from the group consisting of: attention deficit disorder, attention maintenance, eating disorder, weight wellness, depression, anxiety, chronic pain, acute pain, addiction, sleep disorder, iatrogenic pain, Parkinson's, Alzheimer's, hypertension, diabetes, sexual dysfunction, stress and any combination of the foregoing.

10. The device of claim 1, further comprising a resettable lock out feature that permits a predetermined number of uses or hours of usage before the user is locked out from further use.

11. The device of claim 10, wherein the lock out feature can be reset by wired or wireless data transmission.

* * * * *